United States Patent [19]
Bachynsky et al.

[11] Patent Number: 6,149,626
[45] Date of Patent: Nov. 21, 2000

[54] AUTOMATIC INJECTING SYRINGE APPARATUS

[76] Inventors: Nicholas Bachynsky, 701 W. 14th St., Texarkana, Tex. 75501; Arthur A. Alspach, 410 49th St., West Palm Beach, Fla. 33407

[21] Appl. No.: 09/163,417

[22] Filed: Sep. 30, 1998

Related U.S. Application Data

[63] Continuation of application No. 08/943,423, Oct. 3, 1997.

[51] Int. Cl.[7] ........................................... A61M 5/20
[52] U.S. Cl. ........................ 604/134; 604/137; 604/157
[58] Field of Search ................... 604/134, 136, 604/137, 157, 156, 131, 135

[56] References Cited

U.S. PATENT DOCUMENTS

| | | |
|---|---|---|
| 2,549,417 | 4/1951 | Brown . |
| 2,591,046 | 4/1952 | Brown . |
| 3,566,859 | 3/1971 | Schwartz .................................. 604/82 |
| 3,659,749 | 5/1972 | Schwartz . |
| 3,941,130 | 3/1976 | Tibbs . |
| 4,188,950 | 2/1980 | Wardlaw . |
| 4,202,314 | 5/1980 | Smirnov et al. . |
| 4,214,584 | 7/1980 | Smirnov et al. . |
| 4,226,236 | 10/1980 | Genese . |
| 4,261,358 | 4/1981 | Vargas et al. . |
| 4,312,343 | 1/1982 | Leveen et al. . |

(List continued on next page.)

FOREIGN PATENT DOCUMENTS 0072057  2/1983  European Pat. Off. ......... A61M 5/20

OTHER PUBLICATIONS

Hamilton, James G., *The Journal of Family Practice*, vol. 41, No. 2 (Aug.), 1995, pp. 169–175.

Ippolito, Giuseppe et al., *JAMA*, Aug. 24/31, 1994, vol. 272, No. 8, pp. 607–610.

Tereskerz, Patricia M. et al., *The New England Journal of Medicine*, "Occupational Exposure To Blood Among Medical Students", Oct. 10, 1996, vol. 335, No. 15., pp. 1150–1153.

Genotropin™ Brochure, Pharmacia & Upjohn, Inc., 1996, 9 pages.

Cardizem® Lyo–Ject™ Brochure, 4 pages. (No.1.).

The Cardizem® (diltiazem HCl) Lyo–Ject™ Delivery System Brochure, 6 pages.

Cardizem200 Lyo–Ject™ Brochure, 4 pages. (No.1.), 1996.

The Cardizem® (diltiazem HCl) Lyo–Ject™ Delivery System Brochure, pp. 15–20.

*Primary Examiner*—Glenn K. Dawson
*Assistant Examiner*—Jeremy Thissell
*Attorney, Agent, or Firm*—Garvey, Smith, Nehrbass & Doody, L.L.C.

[57] ABSTRACT

A autoinjector type syringe apparatus is provided for injecting a liquid medicine or like into a patient. The apparatus includes a housing that is of two parts including a transversely extending upper housing and a downwardly extending vertically oriented lower housing. A syringe barrel is supported by the housing and has an interior for holding a liquid medicament for being dispensed. A piston is slidably disposed within the interior of the syringe barrel for injecting the medicament from the barrel, the piston being movable between retracting and dispensing positions. A cam member supported by the housing for operating the piston to move between retractive and dispensing positions, the cam being movable between loaded and dispensing positions. The housing includes an upper transversely extending section with an external surface and a cocking mechanism that includes an externally positioned handle that slides on the outer surface of the upper portion of the housing. The handle has a connection with the cam so that when the handle slides upon the upper section, the cam can be cocked into the loaded position. A trigger mechanism releases the cam when the cam is in the loaded position and the trigger is depressed by the user. Springs can be used to bias the cam toward the dispensing position, the springs being stretched when the handle is moved into the cocked position prior to use.

18 Claims, 9 Drawing Sheets

U.S. PATENT DOCUMENTS

| | | |
|---|---|---|
| 4,413,991 | 11/1983 | Schmitz et al. . |
| 4,529,403 | 7/1985 | Kamstra . |
| 4,581,016 | 4/1986 | Gettig .................................. 604/92 |
| 4,583,974 | 4/1986 | Kokernak . |
| 4,613,326 | 9/1986 | Szwarc . |
| 4,792,329 | 12/1988 | Schreuder . |
| 4,861,335 | 8/1989 | Reynolds ............................. 604/191 |
| 4,874,381 | 10/1989 | Vetter . |
| 4,898,580 | 2/1990 | Crowley . |
| 4,968,299 | 11/1990 | Ahlstrand et al. . |
| 4,978,339 | 12/1990 | Labouze et al. . |
| 4,983,164 | 1/1991 | Hook et al. . |
| 4,994,043 | 2/1991 | Ysebaert . |
| 5,041,088 | 8/1991 | Ritson et al. . |
| 5,080,649 | 1/1992 | Vetter . |
| 5,267,963 | 12/1993 | Bachynsky . |
| 5,273,544 | 12/1993 | Van Der Wal . |
| 5,395,326 | 3/1995 | Haber et al. . |
| 5,423,752 | 6/1995 | Haber et al. . |
| 5,695,465 | 12/1997 | Zhu ......................................... 604/89 |
| 5,785,682 | 7/1998 | Graben Kort ........................... 604/82 |
| 5,785,683 | 7/1998 | Szapiro et al. ........................ 604/228 |
| 5,865,804 | 2/1999 | Bachynsky . |

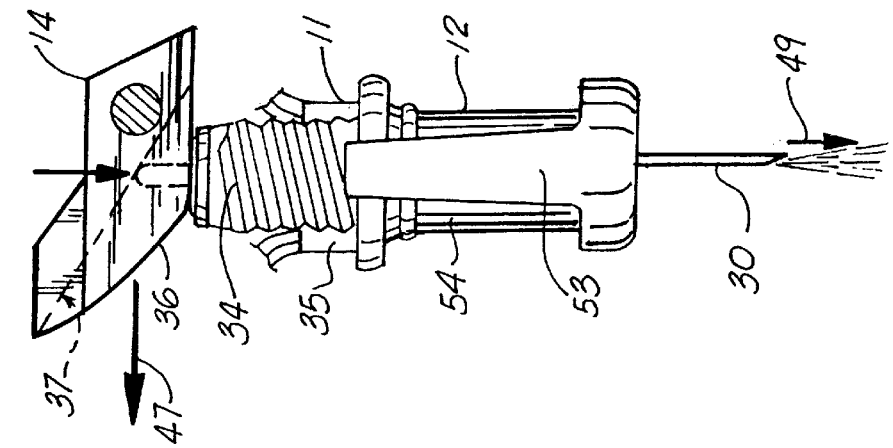
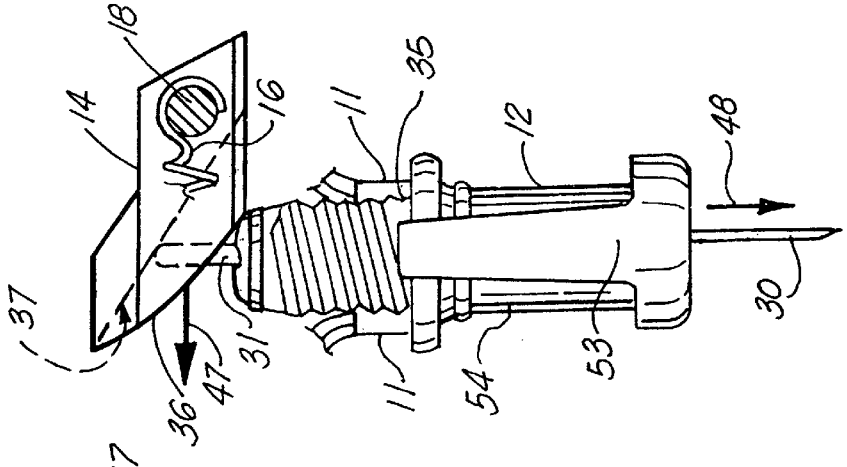
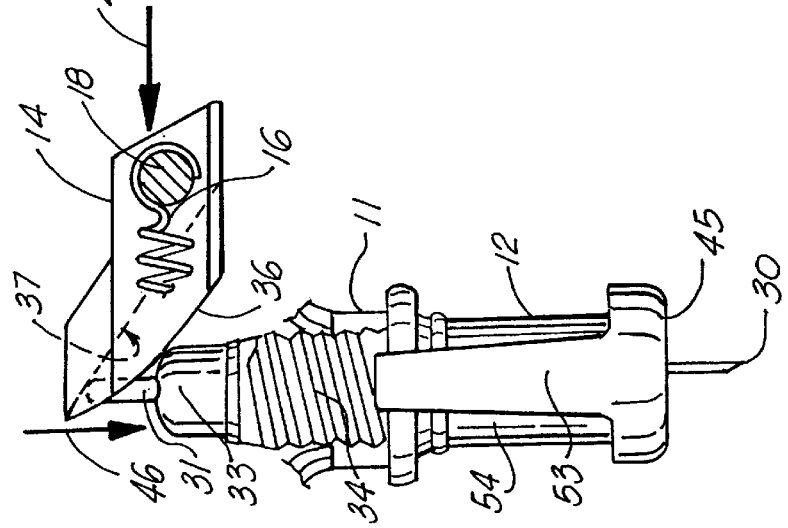

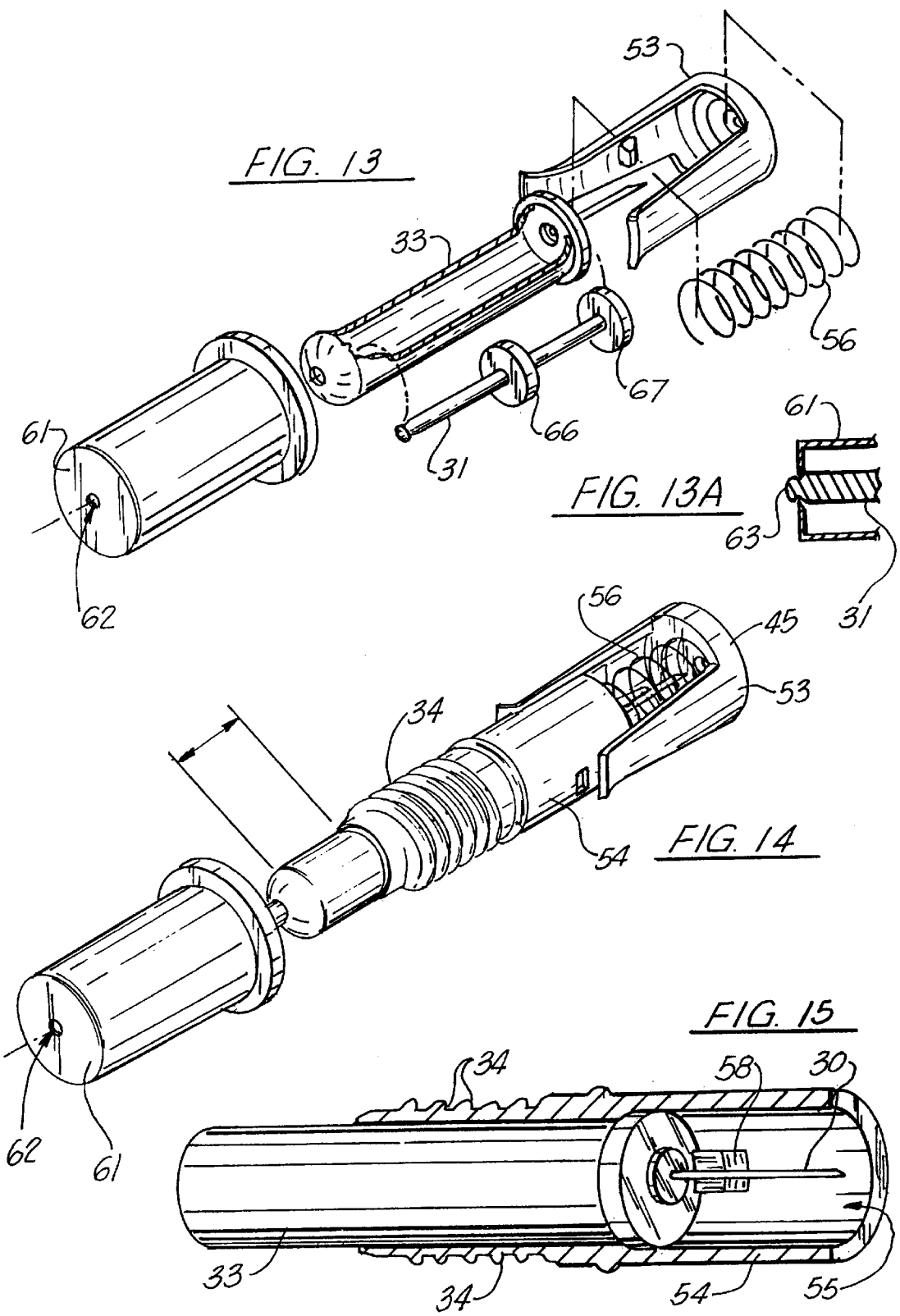

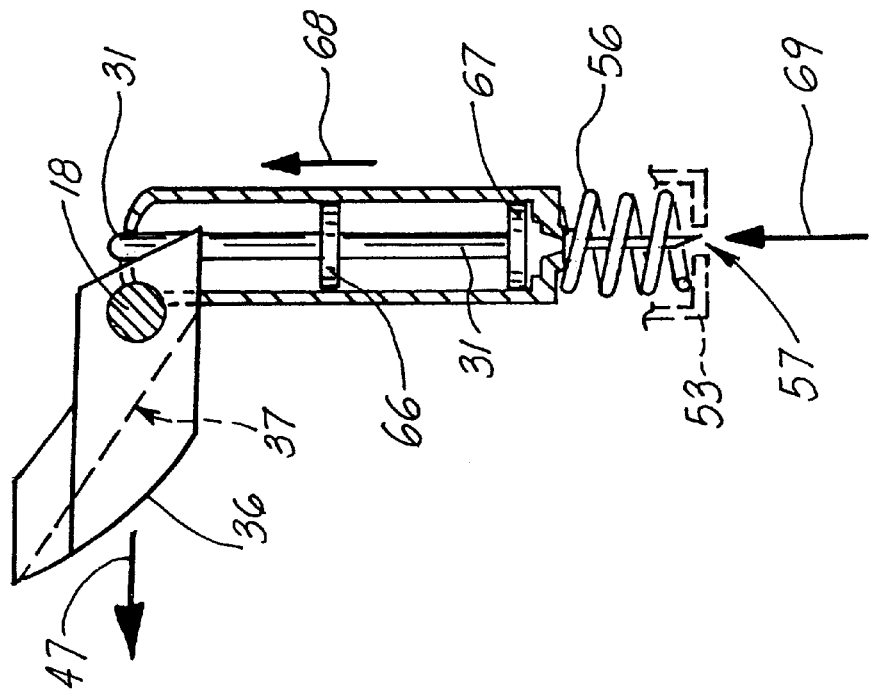
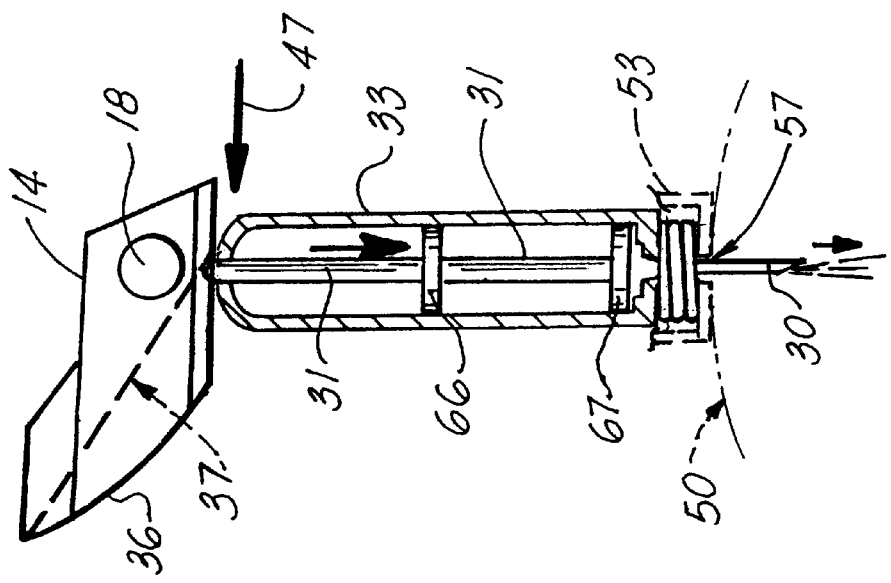

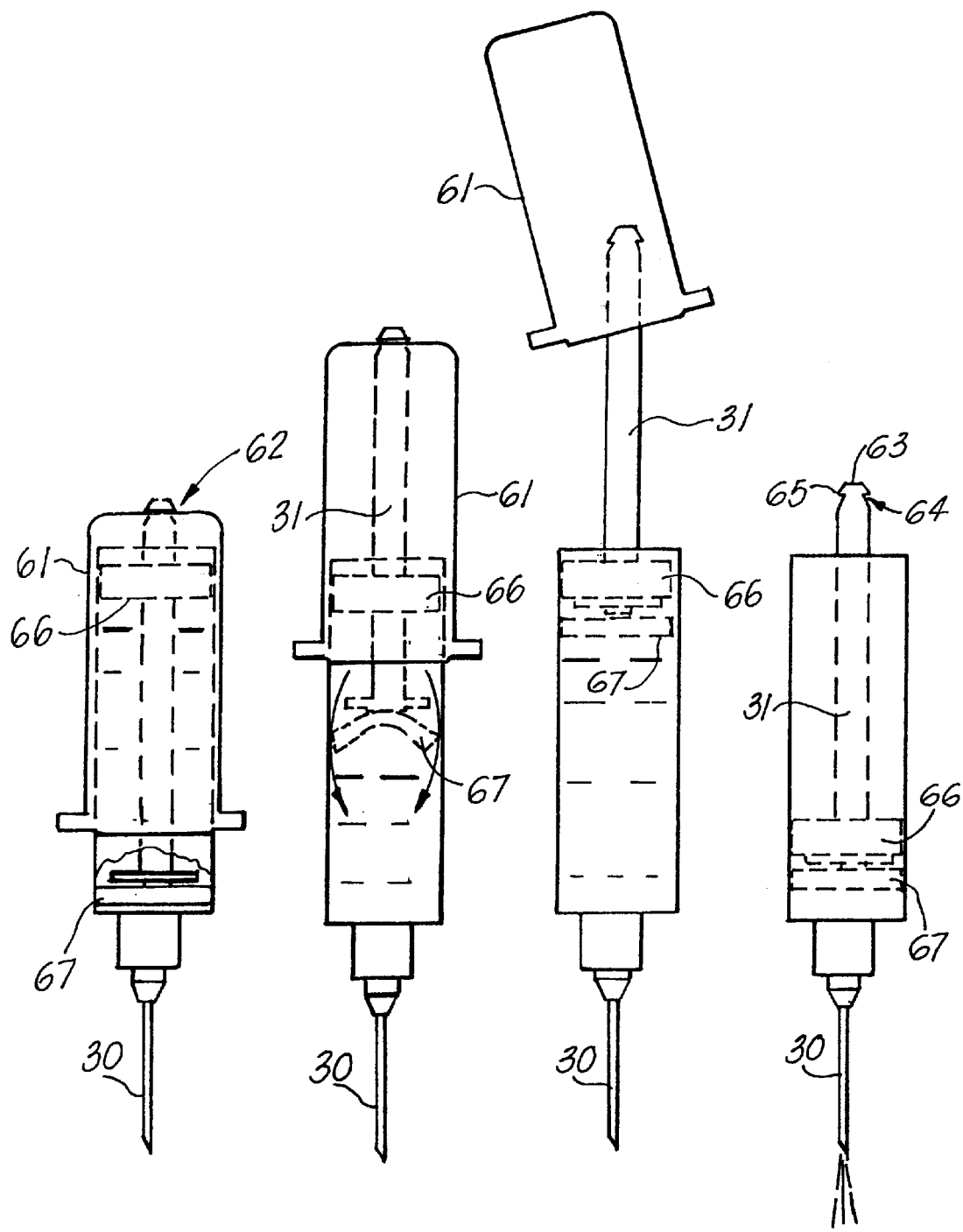

AUTOMATIC INJECTING SYRINGE APPARATUS

CROSS-REFERENCE TO RELATED APPLICATIONS

This is a continuation of co-pending U.S. patent application Ser. No. 08/943,423, filed Oct. 3, 1997, which is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to syringes, and more particularly to an improved reusable autoinjector syringe apparatus. Even more particularly, the present invention relates to an improved auto injector syringe apparatus that accepts disposable syringe cartridges containing a drug or medicament to be dispensed, with a cam arrangement that automatically projects the cartridge needle from a retracted to a projected position into the patient, dispenses the drug or medicament, then retracts the needle.

2. General Background of the Invention

Various forms of spring equipped syringe holders and actuators are known in the art such as the ones shown in my prior U.S. Pat. No. 5,267,963. Other spring equipped syringe holders or actuators include for example U.S. Pat. No. 3,941,130 issued to Tibbs; U.S. Pat. No. 4,261,358 issued to Vargas et al; and U.S. Pat. No. 4,188,950 issued to Wardlaw.

In my prior U.S. Pat. No. 5,267,963, there is provided an automatic injection device which, upon activation by the user, automatically extends a syringe with a needle, delivers medication through the needle and then retracts the needle thus keeping it hidden from view. U.S. Pat. No. 5,267,963 is incorporated herein by reference.

In my prior co-pending patent application Ser. No. 08/943,423, there is provided a dual chamber syringe apparatus that enables a user to reconstitute a drug product that includes a dry portion and a liquid diluent portion.

It is known that many drugs cannot be administered by the oral route because of gastrointestinal intolerance, irregularity in absorption, and metabolic breakdown in the gut wall and liver (first pass effects). In particular, first pass loss abolishes oral bioavailability of all poly-peptide and protein medications [e.g. growth hormone, tumor necrosis factor receptor, insulin, alucaaon, alteplase, erythropoietin, alglucerase (glucocerebrosidase-B-glucosidase), etc.]. This necessitates their administration through various parenteral routes, i.e., intravenous, intramuscular, subcutaneous, intrathecal, etc. Further, parenteral delivery of such drugs will expand with future mapping and functional understanding of the human genome. Pharmaceutical recombinant DNA synthesis of new peptide-protein moieties will concomitantly increase, and make a cost-contained, safe, effective and simple to use delivery device essential for both patients and medical professionals.

Functionally, stability of an injectable drug may be defined as its capability to retain chemical, sterile, toxicological and therapeutic specifications within 90% of its original potency. By tradition, expiration dates denote the last day of a month and year a particular preparation retains such stability under recommended conditions. In case of a dry or lyophilized medication to be reconstituted prior to use, expiration dates are designated for both the dry and reconstituted product. When compared to drug solutions ready for injection, dry soluble medications ready to be reconstituted with solvent just prior to use are well known to have greater stability and longer expiration dates.

Time related deterioration in ready to use parenteral drug preparations include interactions between combined active, and between active and inactive ingredients. Aqueous solvents in particular, potentiated by heat and radiation, initiate or accelerate time dependent degradation through oxidation, reduction, hydrolysis, racemization, decarboxylation, photolysis, and, autooxidative free radical chain reactions.

Notwithstanding such chemical breakdown, buffers, antioxidants, preservatives and other stabilizers oftentimes cannot be used in formulations containing water because of their reactivity with the active ingredient(s) or, direct patient hypersensitivity. Moreover, water itself has a profound effect on hydrolysis and denaturation of drugs possessing ester or amide chemical bonds, e.g. tetracaine, physostigmine, growth hormone, benzylpenicillin, calcitonin, epoetin alfa, menotropins, placental gonadotropin, interferons, pituitary releasing hormones (gonadorelin, cosyntropin, etc.) and numerous others.

A cost effective, simple, self contained dual-chamber syringe which isolates dry-wet drug components and mixes them immediately prior to injection is highly desirable. Furthermore, such a device would eliminate extra standard syringes, medication and diluent containers required for mixing the individual drug constituents. The device would permit accurate drug reconstitution, eliminate waste and possible introduction of contaminants through human error.

An automatic injection type syringe that operates with a disposable cartridge should preferably be configured to function with either a dual chamber or single chamber syringe.

BRIEF SUMMARY OF THE INVENTION

The present invention provides an improved syringe apparatus for injecting or autoinjecting a disposable cartridge that contains a selected medicine to be dispensed into a patient parenterally.

The apparatus of the present invention includes a housing, a syringe cartridge (e.g. disposable) that is supported by the housing which provides an interior for holding a liquid drug or medication to be injected.

A piston is movably disposed within the interior of the syringe barrel for injecting the liquid drug product from the barrel, the piston being movable between retracted and dispensing positions.

A cam is supported by the housing for operating the piston to move between retracted and dispensing positions. The cam is movable between loaded and dispensing positions.

The housing includes an upper transversely extending section with an external surface defining a gripping surface and a mechanism that enables a user to cock the handle into a loaded position. Such a loading pulls the cam laterally away from the syringe barrel and spring loads the cam for storing energy to be used in dispensing.

The handle has a connection with the cam so that when the handle slides upon the upper section of the housing, the cam also moves into a cocked position.

A trigger is provided for releasing the cam when the cam is in the loaded position. The trigger can be finger actuated by the user. Upon depression the trigger releases the cam from the loaded position so that the first or outer cam can engage and depress the syringe barrel. The cam includes a second or inner cam surface that moves the plunger with a needle attached thereto thereby emptying the contents of the syringe. This second cam surface urges the needle outwardly of the lower section of the housing and into the patient. The needle is held in the projected position until the drug product has been dispensed from the barrel and into the patient.

The syringe apparatus of the present invention includes a housing that is configured of two basic parts including an upper section that extends transversely and a lower section that carries the disposable syringe cartridge.

The upper section of the housing has at least one slot that enables a connection to be formed in between the handle and the cam.

In the preferred embodiment, the cartridge has a stop that defines the cartridge position relative to the housing upon assembly.

In the preferred embodiment, the barrel has an externally threaded portion thereon and the housing has an internally threaded portion so that the barrel can form a threaded connection with the housing.

The housing includes an upper section that carries the cam. A trigger is also mounted on the housing. The upper end of the barrel extends into the upper housing section.

The trigger extends from the upper section externally thereof at a position near the barrel to provide a trigger surface for gripping by the user during a firing of the mechanism.

The handle preferably provides a convexly shaped curved surface that extends on opposite sides of the housing for providing a gripping surface to be engaged by the user's hand when cocking the apparatus into the loaded position prior to firing.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 10 is a partial elevational view of a preferred embodiment of the apparatus of the present invention showing the syringe cartridge and cam portions thereof in a cocked, firing position;

FIG. 11 is a partial elevational view of the preferred embodiment of the apparatus of the present invention showing the cam position immediately after firing;

FIG. 12 is a partial elevational view of the preferred embodiment of the apparatus of the present invention showing the cam in a fired position wherein the cartridge is dispensing its contents;

FIG. 13 is a partial perspective fragmentary view of the preferred embodiment of the present invention showing the disposable cartridge portion thereof with the sleeve removed for clarity to show the barrel and plunger;

FIG. 13A is a fragmentary longitudinal sectional view of the cap and plunger;

FIG. 14 is a fragmentary perspective view of the preferred embodiment of the present invention showing the disposable cartridge portion thereof;

FIG. 15 is a fragmentary partial sectional view of the disposable cartridge of the preferred embodiment of the apparatus of the present invention;

FIGS. 16–20 are schematic elevational cutaway views illustrating operation of the preferred embodiment of the apparatus of the present invention and particularly the cam and disposable cartridge portions thereof; and FIGS. 21–24 are sequential schematic views that illustrate the adjustable cap portion of the present invention.

DETAILED DESCRIPTION OF THE INVENTION

Figure 1:
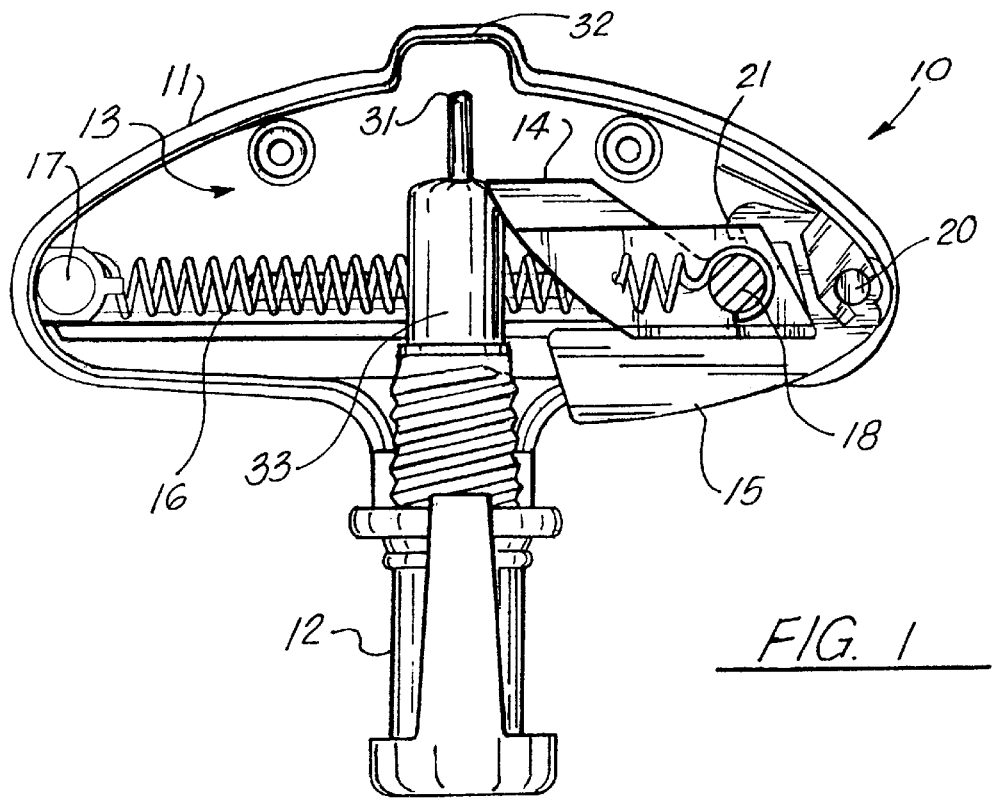
FIG. 1 is a sectional elevational view of the preferred embodiment of the apparatus of the present invention.

FIGS. 1–7 show generally the preferred embodiment of the apparatus of the present invention designated generally by the numeral 10 in FIGS. 1–7. Syringe apparatus 10 provides an overall housing that is comprised of upper housing section 11 and lower housing section 12. Upper housing 11 section has an interior 13 that carries a cam 14, trigger mechanism 15, spring 16, and the upper portion of syringe barrel 33.

Spring 16 extends between spring anchor 17 and the cam 14. When the cam 14 is moved to a cocked position (see FIGS. 4 and 10), it is spring loaded for firing. In the preferred embodiment, a pair of springs 16 can be provided, each being associated with an appendage 18, 19. Appendages 18, 19 extend from cam 14 as shown in FIGS. 1–2, 7–9, and 10–12.

Figure 4:
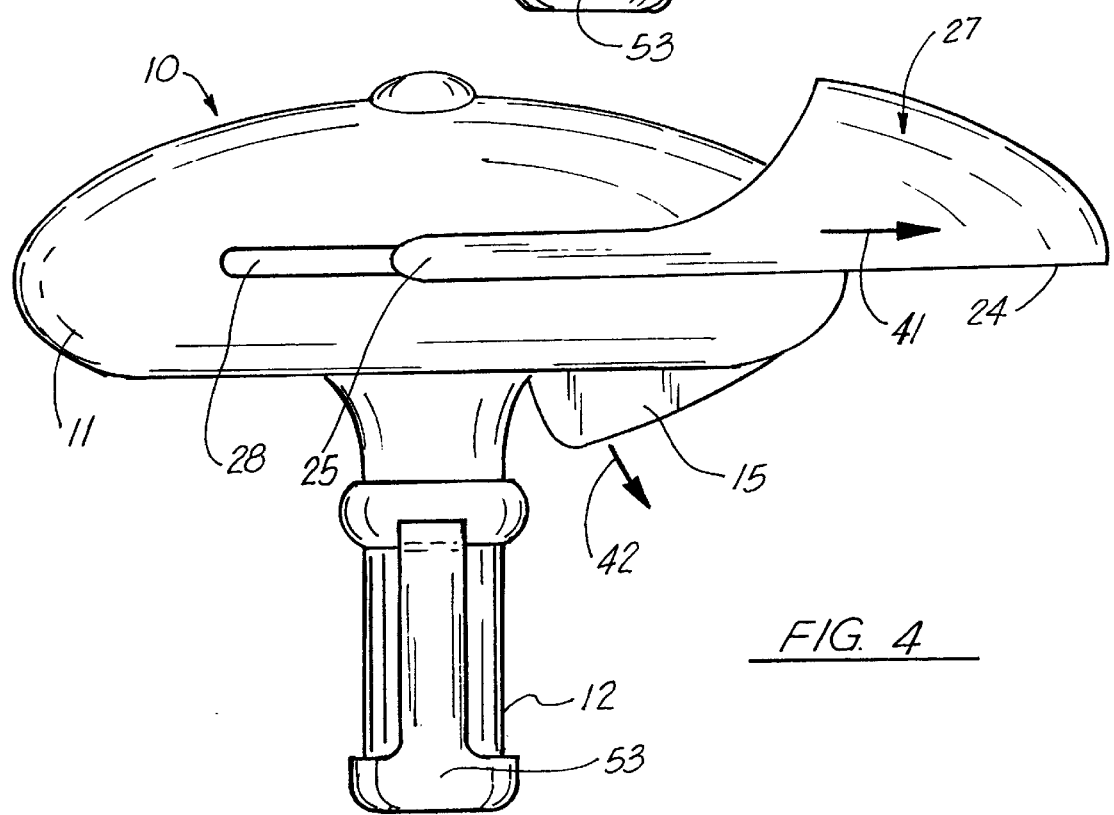
FIG. 4 is an elevational view of the preferred embodiment of the apparatus of the present invention showing the handle in a cocked, firing position.
Figure 5:
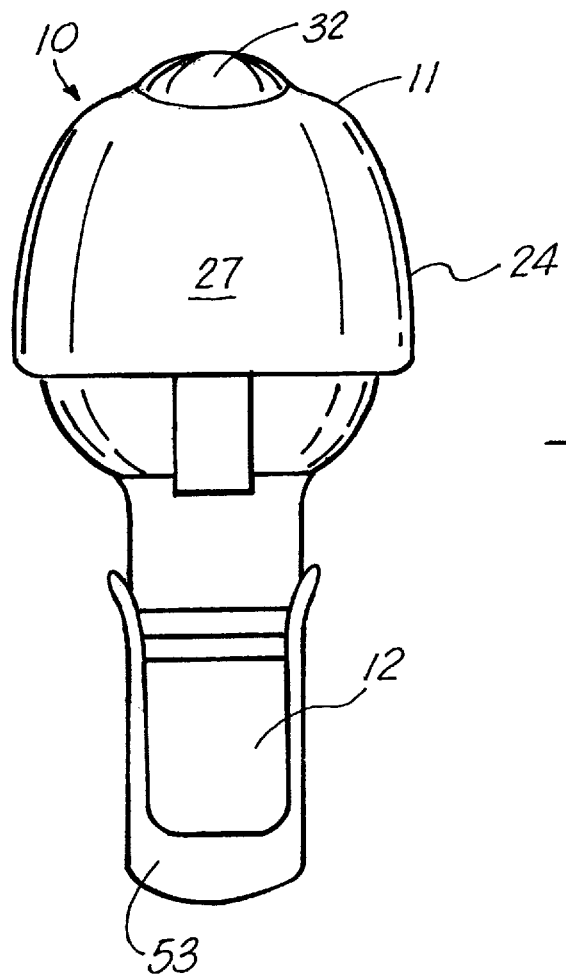
FIG. 5 are opposing side elevational views of the preferred embodiment of the apparatus of the present invention.
Figure 6:
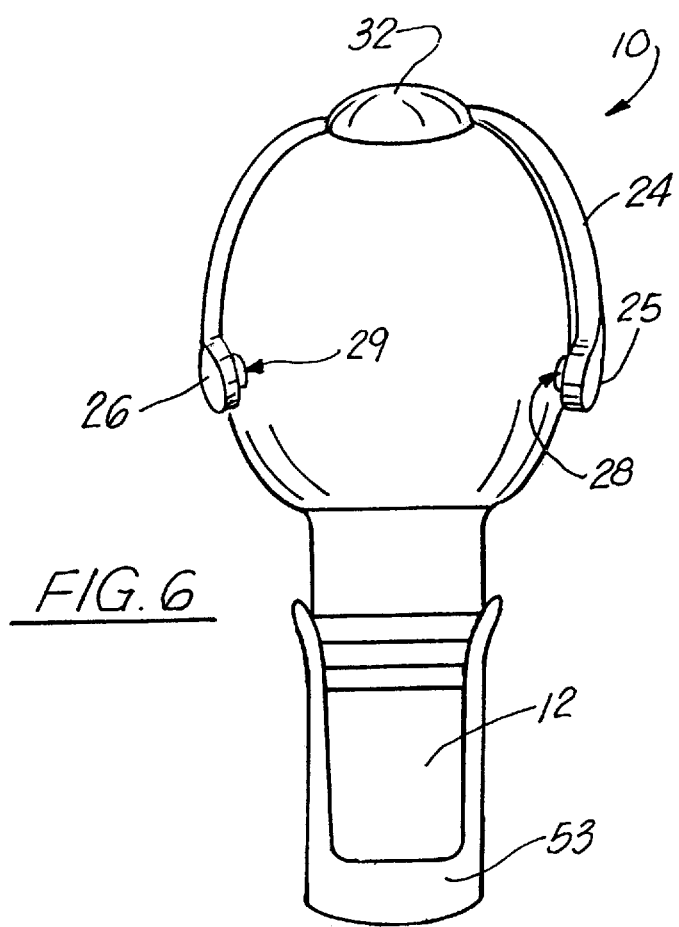
FIG. 6 are partial side elevational views of the preferred embodiment of the apparatus of the present invention illustrating connection of the cartridge and spring retainer.
Figure 7:
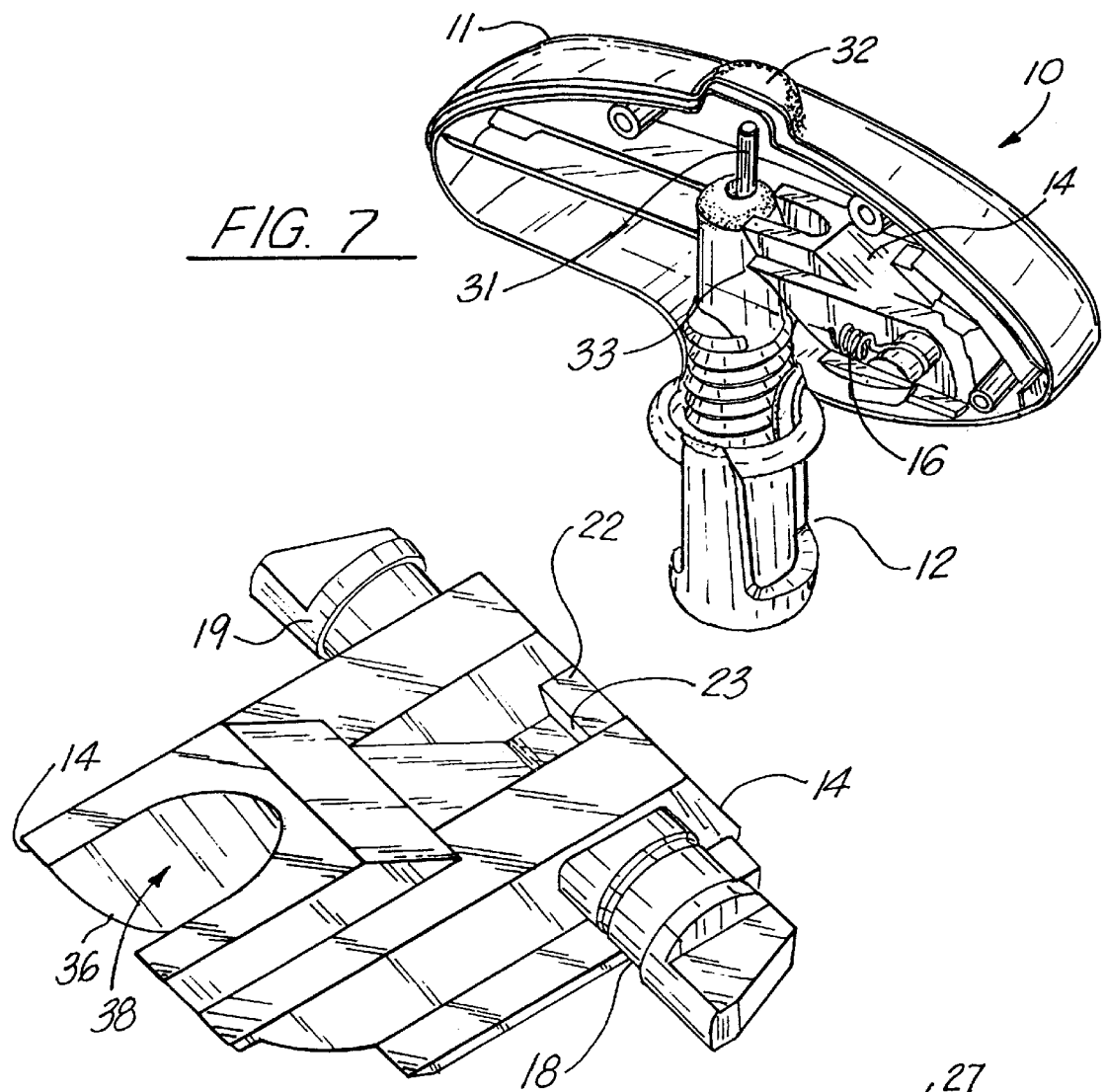
FIG. 7 is a perspective cutaway of the preferred embodiment of the apparatus of the present invention.
Figure 8:
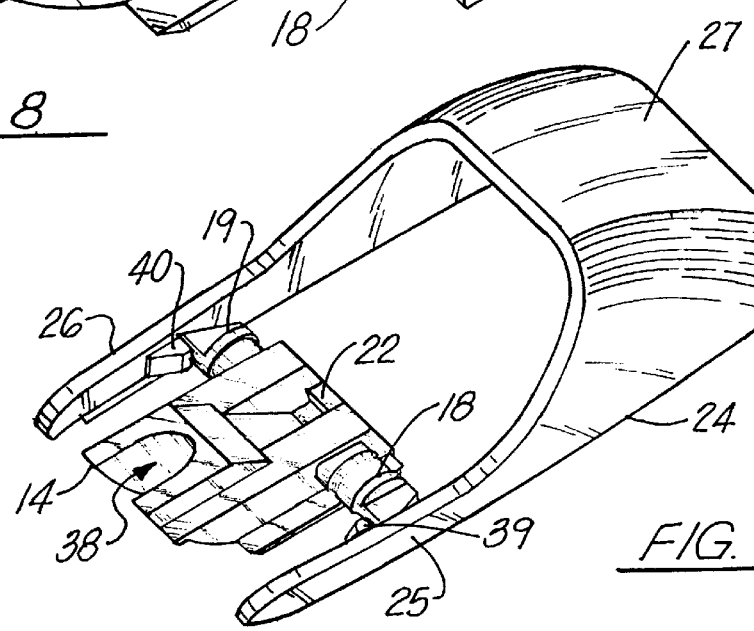
FIG. 8 is a fragmentary perspective view of the preferred embodiment of the apparatus of the present invention showing the cam portion thereof.

Trigger mechanism 15 is pivotally mounted upon pivot 20. The trigger 15 is movable between a first loaded position as shown in FIGS. 1, 4, and 10 and a second firing position as shown in FIGS. 2, 3, and 11–12. In order to fire the apparatus 10, a user squeezes the trigger 15 upwardly in order to disengage sear 21 from transverse member 22 of cam 14. More particularly, the sear 21 disengages from vertical surface 23 of transverse member 22 on cam 14 in order to fire the apparatus 10. A return spring can be provided for urging trigger 15 into the locked position shown in FIG. 1 wherein the sear 21 engages transverse member 22 and surface 23.

Handle 24 is provided for moving the cam 14 into the loaded, pre-firing position of FIGS. 1, 4, and 10. In order to move the cam 14 into the loaded position, a user grips handle 24 at the gripping surface 27 thereon and moves handle 24 laterally as shown by arrow 41 in FIG. 4. This action also enables the spring loaded trigger 25 to move downwardly as shown by arrow 42 in FIG. 4. When the handle 24 is moved to the loaded position, sear 21 engages vertical surface 23 of transverse member 22 as shown in FIG. 1, holding the cam 14 in the position of FIG. 1 so that the cam is spring loaded and ready to fire.

Figure 2:
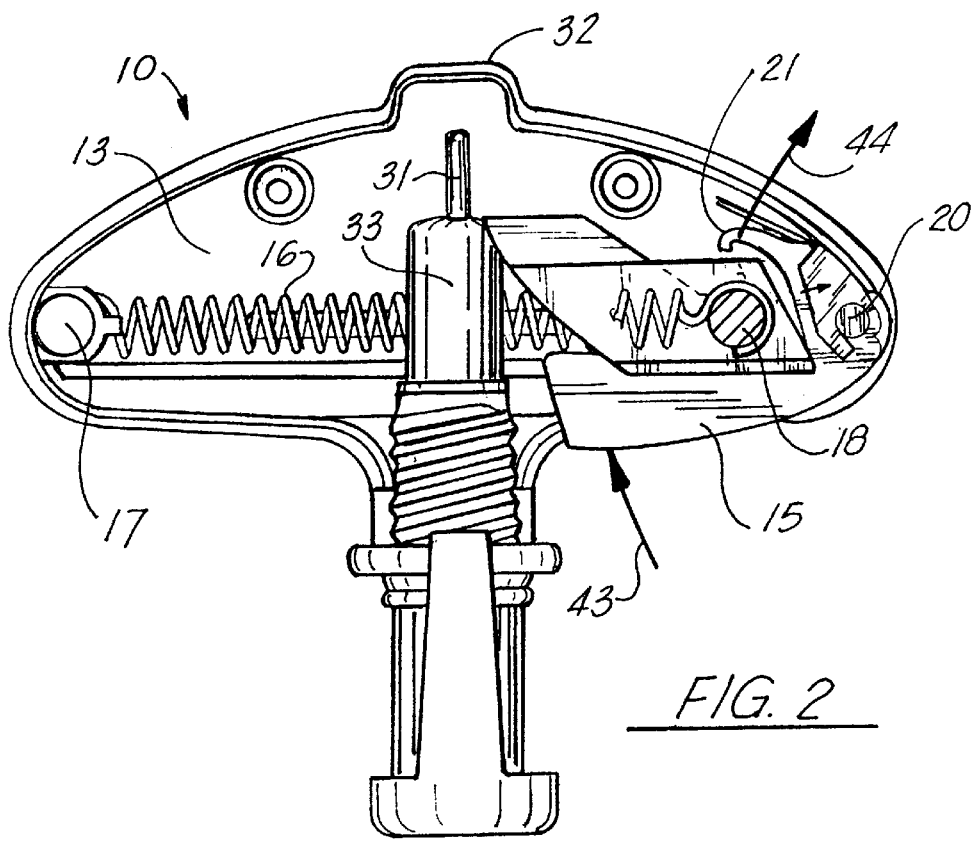
FIG. 2 is a sectional elevational view of the preferred embodiment of the apparatus of the present invention showing the trigger in a firing position.
Figure 3:
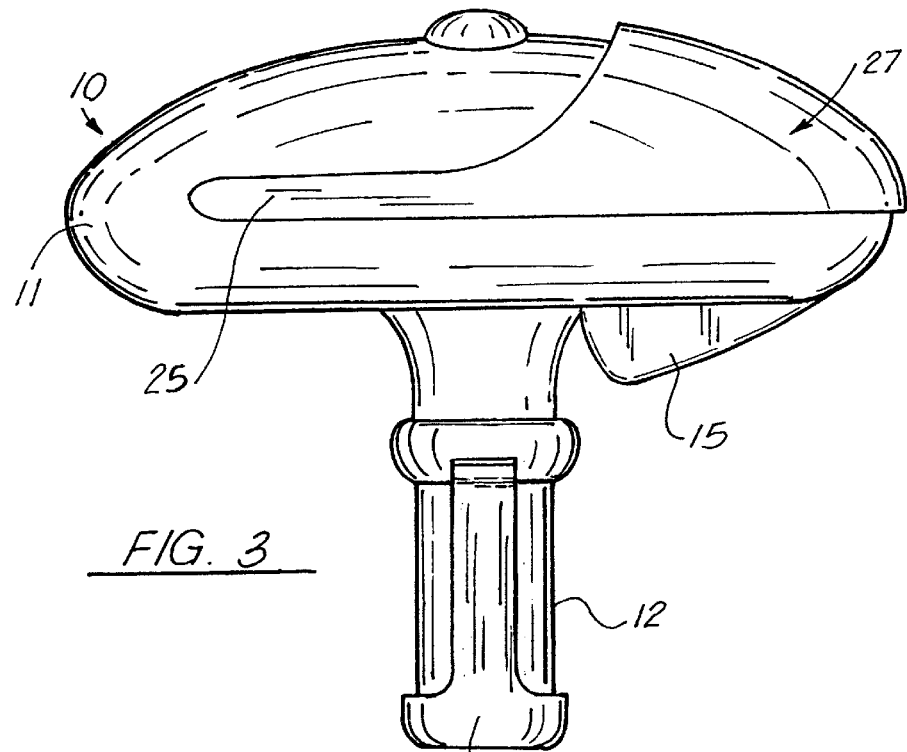
FIG. 3 is an elevational view of the preferred embodiment of the apparatus of the present invention shown prior to a movement of the handle into the cocked, firing position.

In FIG. 2, a user has moved the trigger 15 upwardly as shown by arrow 43. Sear 21 also moves upwardly as shown by arrow 44 in FIG. 2 in order to fire the apparatus 10. This action releases the sear 21 from spring loaded cam 14, allowing cam 14 to move toward barrel 33 (see FIGS. 16–18). Spring 16 pulls the cam 14 toward barrel 33. This action is shown by the initial position of cam 14 in FIGS. 10 and 16, the intermediate position of cam 14 in FIG. 11, and a final dispensing and injection position of cam 14 in FIGS. 12 and 18.

Figure 9:
FIG. 9 is a partial perspective view of the preferred embodiment of the apparatus of the present invention illustrating the cam and handle portions thereof.

The handle 24 provides a pair of side portions 25, 26 as shown in FIG. 9. Each of the side portions 25, 26 provides a lug 39, 40 for forming an attachment to the laterally extending appendages 18, 19 of cam 14. In FIG. 9, lug 39 engages appendage 18 of cam 14. Lug 40 engages appendage 19 of cam 14. The lugs 39, 40 enable a connection to be formed between cam 14 and handle 24. In this manner, when the user pulls the handle 24 toward the firing position, cam 14 travels with it and stretches spring(s) 16 in order to load the device 10. A pair of opposed slots 28, 29 are provided in upper housing section 11 as shown in FIGS. 3–6 for enabling the lugs 39, 40 to extend through the wall of upper section 11 in order to communicate with the interior 13 thereof and engage appendages 18, 19.

FIGS. 1–6A and 10–15 illustrate the construction of lower housing section 12. Dome 32 of upper housing section 11 accommodates plunger 31 when plunger 31 is in the full up position of FIGS. 1 and 16. Needle 30 extends through opening 62 in cap 61 externally thereof as cam 14 advances and engages the top of barrel 13 with first cam surface 36. A second cam surface 37 is provided for engaging plunger 31 of barrel 33.

In FIGS. 13–15 and 21–24, lower housing 12 includes barrel 33 supported by sleeve 54 that is covered with cap 61 as shown in FIGS. 14–15. Cap 61 has internal threads that engage the external threads 34 on sleeve 54. Plunger 31 has an end portion with annular groove 64 and annular shoulder 65 so that the plunger 31 can grip and connect removably to cap 61 at opening 62 as shown in FIGS. 21 and 22 (see FIGS. 13A and 24). During use, the user can mix the clay contents of a dual chamber cartridge with selected amount of diluent. An adjustable mix is achieved by threading cap 61 upon threads 34 of sleeve 54 to vary the distance that plunger 31 travels during mixing. In FIG. 22 for example, cap 61 has been moved (by rotating cap 61 in a counter-clockwise direction) only a partial distance of the travel of plunger 31. At this-point, cap 61 could be removed by separating shoulder 65 and groove 64 from opening 62. However, in FIG. 23, cap 61 was rotated until plunger 31 was fully open.

Sleeve 54 has a bore 55 that holds barrel 33. In FIGS. 10–12, lower housing 11 has internal threads 35 that are engaged by the external threads 34 of sleeve 54 once cap 61-has been removed. Lugs 58 on spring holder 53 engage lugs 59 on sleeve 54 upon assembly. Sleeve 54 thus supports spring holder 53. Spring 56 fits in between spring holder 53 and barrel 33.

During use, barrel 33 slides up and down with respect to sleeve 54 and spring holder 53. Spring holder 53 has an opening 57 through which needle 30 passes during an intravenous injection (see FIGS. 10–12 and 16–20). A stop can be provided on sleeve 54 to limit downward travel of barrel 33 during use.

Figure 18:
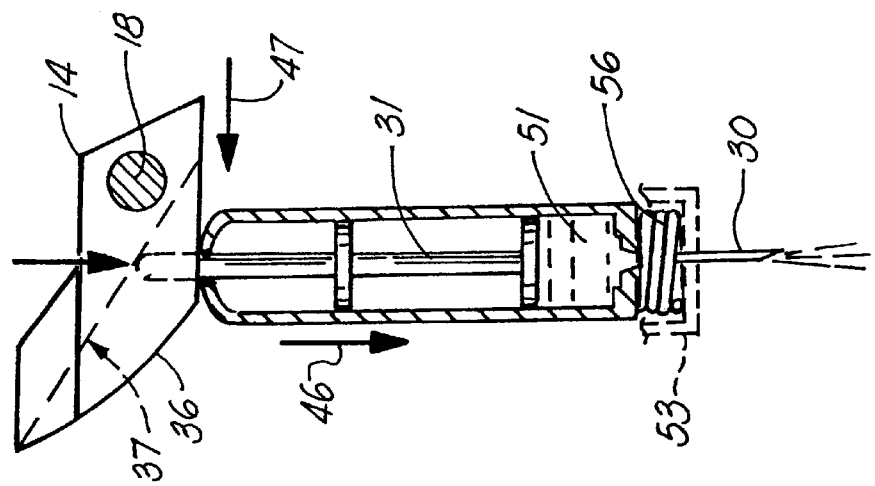
Figure 17:
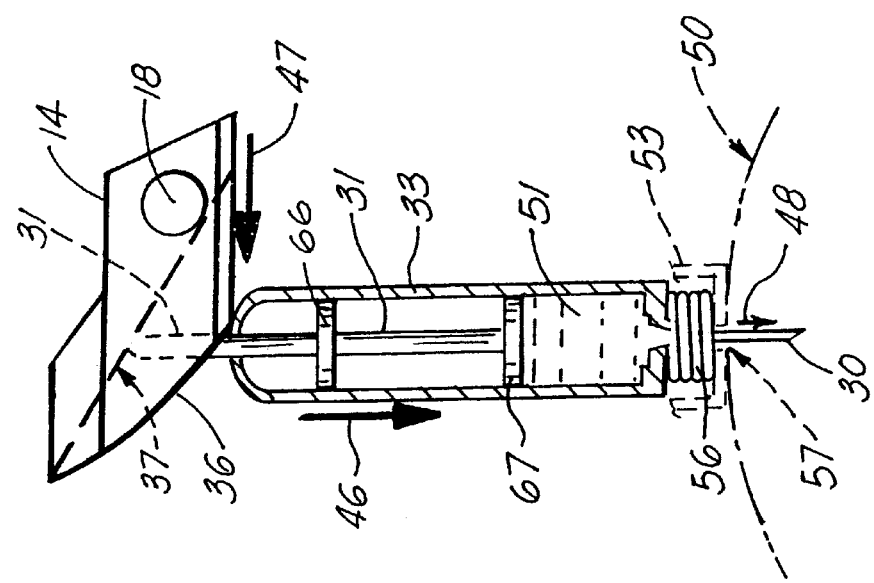
Figure 16:
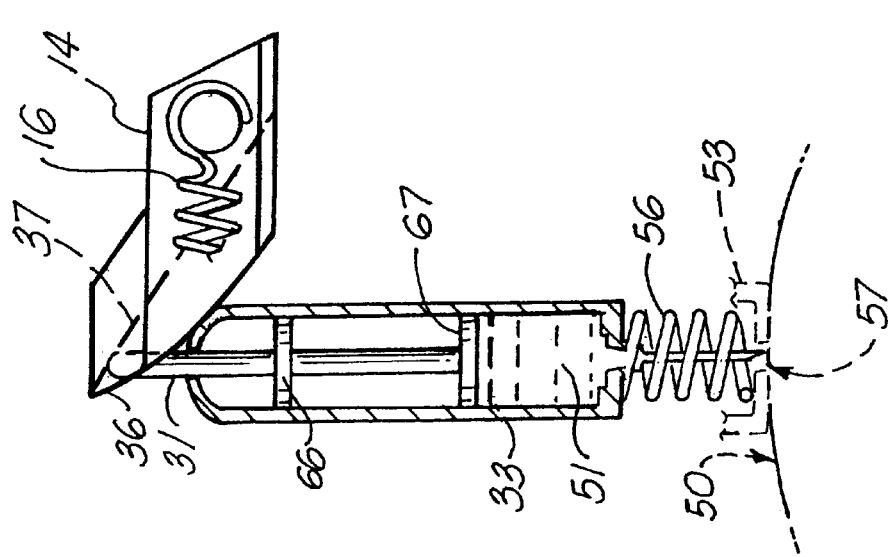

After the device 10 is fired, first cam surface 36 engages the top of barrel 33 and urges the entire barrel downwardly together with needle 30. This action causes the needle 30 to protrude slightly below the lower surface 45 of lower housing section 12. If the surface 45 is placed against a patient's skin, the needle 30 penetrates the patient's skin 50 as first cam surface 36 engages the upper end of barrel 33 as shown in FIGS. 10 and 16–17. This movement of barrel 33 downwardly is indicated schematically by the arrow 46 in FIGS. 10 and 17–18. Lateral movement of cam 14 is indicated by arrow 47 in FIGS. 10–12 and 17–20. Continued lateral movement in the direction of arrow 47 causes second cam surface 37 to engage plunger 31 as shown in FIGS. 11 and 17–18. By the time that second cam surface 37 reaches plunger 31, first cam surface 36 has fully urged barrel 33 to its lowermost position, fully exposing needle 30. This downward movement of needle 30 is indicated by the arrow 48 in FIGS. 11 and 17.

In FIGS. 12 and 18, second cam surface 37 has fully depressed plunger 31. This engagement of plunger 31 by second cam surface 37 causes the plunger 31 to dispense the medicinal contents 51 of barrel 33 as schematically indicated by the arrow 49 in FIG. 12. A gap 38 can be seen at the front of cam 14 for receiving plunger 31. In this fashion, the plunger 31 enters the gap while the cam surfaces 36 are forcing barrel 33 downwardly.

FIGS. 19 and 20 show a retraction of needle 30 after the medicine or drug 51 has been fully dispensed into the patient. In FIG. 19, the cam surface 37 has fully depressed plunger 31 and all of the contained medicine 51 has been intravenously injected into the patient. Continued movement of the cam 14 causes the cam surface 37 to pass beyond plunger 31 so that return spring 56 can push the plunger 31 upwardly in the direction of arrow 68 as shown in FIG. 20. The return spring 56 thus moves the plunger 31 upwardly and retracts the needle 30 into needle holder 53 as shown by arrows 69 in FIG. 20.

In FIGS. 21–24, a dual chamber syringe is shown in use with protective cap 61. The plunger 31 has a forward seal 67 that is a flexible seal. The forward seal 67 flexes during a mixing of liquid diluent and dry medicine. The seal 66 is a floating rear seal that moves with respect to plunger 31 as liquid diluent is mixed with the dry medicine that is preliminarily contained below forward seal 67. As the forward seal 67 flexes (see FIG. 22), liquid diluent flows around the seal 67 and below it to mix with the dry medicine. After all of the liquid diluent has been mixed, the two seals 66, 67 abut one another as shown in FIG. 23. The protective cap 61 is removed as shown in FIG. 23 once a desired degree of mixing occurs. The syringe is then ready for dispensing with the apparatus 10 of the present invention for auto injection.

It should be understood that a barrel and plunger arrangement as seen in FIGS. 21–24 in the form of a disposable cartridge can preferably be of the type shown and described more particularly in my prior co-pending patent application Ser. No. 08/943,423, filed Oct. 3, 1997, and entitled "Improved Dual Chamber Syringe Apparatus", incorporated herein by reference.

The following table lists the parts numbers and parts descriptions as used herein and in the drawings attached hereto.

PARTS LIST

| Part Number | Description |
|---|---|
| 10 | syringe apparatus |
| 11 | upper housing |
| 12 | lower housing |
| 13 | interior |
| 14 | cam |
| 15 | trigger |
| 16 | spring |
| 17 | spring anchor |
| 18 | appendage |
| 19 | appendage |
| 20 | pivot |
| 21 | sear |
| 22 | transverse member |
| 23 | vertical surface |
| 24 | handle |
| 25 | side |
| 26 | side |
| 27 | gripping surface |
| 28 | slot |
| 29 | slot |
| 30 | needle |
| 31 | plunger |
| 32 | dome |
| 33 | barrel |
| 34 | external threads |
| 35 | internal threads |
| 36 | first cam surface |
| 37 | second cam surface |
| 38 | gap |
| 39 | lug |
| 40 | lug |
| 41 | arrow |
| 42 | arrow |
| 43 | arrow |
| 44 | arrow |
| 45 | lower surface |
| 46 | arrow |
| 47 | arrow |
| 48 | arrow |
| 49 | arrow |
| 50 | patient's skin |
| 51 | medicine |
| 53 | spring holder |
| 54 | sleeve |
| 55 | bore |
| 56 | return spring |
| 57 | opening |
| 58 | lug |
| 59 | lug |
| 62 | opening |
| 63 | plunger upper end |
| 64 | annular groove |
| 65 | annular shoulder |
| 66 | floating rear seal |
| 67 | forward seal |
| 68 | arrow |
| 69 | arrow |

The foregoing embodiments are presented by way of example only; the scope of the present invention is to be limited only by the following claims.

What is claimed is:

1. A syringe apparatus for injecting a medicament, comprising:
   a) a housing;
   b) a syringe barrel supported by the housing and having an interior for holding said medicament;
   c) a piston movably disposed within the interior of the syringe barrel for ejecting the medicament from the barrel, the piston being movable between retracted and dispensing positions;
   d) a cam supported by the housing for operating the piston to move between retracted and dispensing positions, the cam being movable between loaded and dispensing positions;
   e) the housing including an upper transversely extending section with an external surface and a cocking mechanism that includes an externally positioned handle that is curved to extend to opposite sides of the housing and that slides on the outer surface of the upper section;
   f) the handle having a connection with the cam so that when the handle slides upon the upper section, the cam can be cocked into the loaded position; and
   g) a trigger for releasing the cam when the cam is in the loaded position.

2. The syringe apparatus of claim 1 wherein the upper section of the housing has a pair of slots that enable a connection to be formed between the handle and cam.

3. The syringe apparatus of claim 1 wherein the barrel has a stop that defines its position relative to the housing.

4. The syringe apparatus of claim 1 wherein the barrel has an externally threaded portion thereon and the housing has an internally threaded portion so that the barrel can form a threaded connection with the housing.

5. The syringe apparatus of claim 1 wherein the housing upper section contains the cam, the trigger and the upper end of the barrel, the trigger extending from the upper section at a position near the barrel.

6. The syringe apparatus of claim 1 wherein the handle had a generally U-shaped cross section.

7. The syringe apparatus of claim 1 wherein the handle extends over the top of the upper transversely extending section.

8. The syringe apparatus of claim 1 wherein the housing upper section is hollow and contains the cam, at least part of the trigger and the upper end of the barrel, the trigger extending from the upper section at a position near the barrel.

9. A syringe apparatus for injecting a medicament, comprising:
   a) housing:
   b) a syringe barrel supported by the housing and having an interior for holding said medicament;
   c) a piston movably disposed within the interior of the syringe barrel for ejecting the medicament from the barrel, the piston being movable between retracted and dispensing portions;
   d) a cam supported by the housing for operating the piston to move between retracted and dispensing positions, the cam being movable between loaded and dispensing positions;
   e) the housing including an upper transversely extending section with an external surface and a cocking mechanism that includes an externally positioned handle that slides on the outer surface of the upper section;
   f) the handle having a connection with the cam so that when the handle slides upon the upper section, the cam can be cocked into the loaded position;
   g) a trigger for releasing the cam when the cam is in the loaded position;
   h) wherein the upper section of the housing has at least one slot that enables a connection to be formed between the handle and cam; and
   wherein there are a pair of opposed slots that enable a connection to be formed between the handle and the cam.

10. A syringe apparatus for injecting a medicament, comprising:
 a) a housing;
 b) a syringe cartridge that includes an outer barrel and a piston, said cartridge being removably supported by the housing and having an interior for holding said medicament;
 c) said piston movably disposed within the interior of the syringe barrel for ejecting the medicament from the barrel, the piston being movable between retracted and dispensing positions;
 d) a cam supported by the housing for operating the piston to move between retracted and dispensing positions, the cam being movable between loaded and dispensing positions;
 e) the housing including an upper transversely extending section with an external surface, a hollow interior, and a cocking mechanism that includes an externally positioned handle that is curved to extend to opposite sides of the housing and that slides on the external surface of the upper section;
 f) the handle having a connection with the cam so that when the handle slides upon the upper housing section, the cam can be moved into the loaded position; and
 g) a trigger mechanism for holding the cam in the loaded position and for selectively releasing the cam by operating the trigger when the cam is in the loaded position.

11. The syringe apparatus of claim 10 wherein the upper section of the housing has a pair of slots, and lugs on the handle extend through the slot defining a connection formed between the handle and cam.

12. The syringe apparatus of claim 11 wherein there are a pair of opposed slots that enable a connection to be formed between the handle and the cam.

13. The syringe apparatus of claim 10 wherein the cam has at least one appendage to which springs are attached for biasing the cam.

14. The syringe apparatus of claim 13 wherein there are a pair of springs.

15. The syringe apparatus of claim 10 wherein the barrel has a stop that defines the position of the cartridge relative to the housing.

16. The syringe apparatus of claim 10 wherein the barrel has an externally threaded portion thereon and the housing has an internally threaded portion so that the barrel can form a threaded connection with the housing.

17. The syringe apparatus of claim 10 wherein the handle had a generally U-shaped cross section.

18. The syringe apparatus of claim 10 wherein the cam has two cam surfaces for independently moving the barrel and the plunger.

* * * * *